US012433520B2

(12) United States Patent
Ivosevic et al.

(10) Patent No.: US 12,433,520 B2
(45) Date of Patent: Oct. 7, 2025

(54) ARTERIAL BLOOD GAS COLLECTION SYSTEM

(71) Applicant: Becton, Dickinson and Company, Franklin Lakes, NJ (US)

(72) Inventors: Milan Ivosevic, Kinnelon, NJ (US); Alexander James Blake, Ridgewood, NJ (US); Anthony V. Torris, Montclair, NJ (US); Michael Vincent Quinn, Gladstone, NJ (US); Richard A. Cronenberg, Gladstone, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 406 days.

(21) Appl. No.: 17/272,767

(22) PCT Filed: Sep. 5, 2019

(86) PCT No.: PCT/US2019/049680

§ 371 (c)(1),
(2) Date: Mar. 2, 2021

(87) PCT Pub. No.: WO2020/051289

PCT Pub. Date: Mar. 12, 2020

(65) Prior Publication Data

US 2021/0315498 A1 Oct. 14, 2021

Related U.S. Application Data

(60) Provisional application No. 62/727,869, filed on Sep. 6, 2018.

(51) Int. Cl.
*A61B 5/15* (2006.01)
*A61B 5/153* (2006.01)

(52) U.S. Cl.
CPC .... *A61B 5/150755* (2013.01); *A61B 5/15003* (2013.01); *A61B 5/150213* (2013.01);
(Continued)

(58) Field of Classification Search
CPC .............................. A61B 5/15–150045; A61B 5/150213–150267;
(Continued)

(56) References Cited

U.S. PATENT DOCUMENTS 4,595,021 A 6/1986 Shimizu et al.
5,057,089 A 10/1991 Greco
(Continued)

FOREIGN PATENT DOCUMENTS

CN 2875456 Y 3/2007
EP 1221303 A2 * 7/2002 ........... A61B 5/1405
(Continued)

*Primary Examiner* — Jennifer Robertson
*Assistant Examiner* — Om Patel
(74) *Attorney, Agent, or Firm* — The Webb Law Firm

(57) ABSTRACT

An arterial blood module (16) that is removably connectable to an arterial blood collection element (14) is disclosed. The arterial blood module includes a housing (30), a needle (32), a cap (34) removably securable over the needle, a mixing chamber (36), and a safety shield (38) engaged with a portion of the housing and transitionable from a first shield position in which a portion of the needle is exposed to a second shield position in which the needle is shielded by a portion of the safety shield. In one embodiment, the present disclosure includes an arterial blood collection system (10) that includes an arterial blood collection element (14) defining a collection chamber (20) and an arterial blood module (16) removably connectable to a portion of the arterial blood collection element.

29 Claims, 17 Drawing Sheets

(52) U.S. Cl.
CPC .. *A61B 5/150221* (2013.01); *A61B 5/150236* (2013.01); *A61B 5/150244* (2013.01); *A61B 5/150259* (2013.01); *A61B 5/150389* (2013.01); *A61B 5/150633* (2013.01); *A61B 5/153* (2013.01)

(58) Field of Classification Search
CPC ..... A61B 5/150374–150396; A61B 5/150412; A61B 5/150427; A61B 5/150503–150572; A61B 5/150633–150725; A61B 5/150755; A61B 5/153; A61B 5/1535
See application file for complete search history.

(56) References Cited

U.S. PATENT DOCUMENTS

| | | | | |
|---|---|---|---|---|
| 5,086,783 | A | 2/1992 | Macors et al. | |
| 5,893,834 | A | 4/1999 | Duchamp | |
| 5,921,964 | A | 7/1999 | Martin | |
| 6,183,445 | B1 | 2/2001 | Lund et al. | |
| 6,511,439 | B1 | 1/2003 | Tabata et al. | |
| 6,629,957 | B1 | 10/2003 | Wiklund | |
| 6,629,959 | B2 | 10/2003 | Kuracina et al. | |
| 6,860,871 | B2 | 3/2005 | Kuracina et al. | |
| 6,869,415 | B2 | 3/2005 | Asbaghi | |
| 7,211,065 | B2 | 5/2007 | Miller | |
| 7,329,238 | B2 | 2/2008 | Halseth et al. | |
| 7,393,345 | B2 | 7/2008 | Yang | |
| 8,545,454 | B2 | 10/2013 | Kuracina et al. | |
| 8,663,129 | B2 | 3/2014 | Allen et al. | |
| 9,283,329 | B2 | 3/2016 | Perez | |
| 9,320,469 | B2 | 4/2016 | Shaw et al. | |
| 9,445,760 | B2 | 9/2016 | Allen et al. | |
| 9,532,742 | B2 | 1/2017 | Hoong Sim et al. | |
| 9,533,108 | B2 | 1/2017 | Salto et al. | |
| 9,642,569 | B2 | 5/2017 | Neo et al. | |
| 9,687,184 | B2 | 6/2017 | Crawford et al. | |
| 9,694,140 | B2 | 7/2017 | Rubinstein et al. | |
| 9,770,200 | B2 | 9/2017 | Schraga | |
| 9,848,810 | B2 | 12/2017 | Allen et al. | |
| 9,986,943 | B2 | 6/2018 | Zakaria et al. | |
| 10,179,211 | B2 | 1/2019 | Rozwadowski et al. | |
| 10,335,554 | B2 | 7/2019 | Rubinstein et al. | |
| 10,518,045 | B2 | 12/2019 | Calvert | |
| 11,103,651 | B2 | 8/2021 | Sanders et al. | |
| 2004/0133172 | A1 * | 7/2004 | Wilkinson ....... | A61B 5/150572 604/263 |
| 2006/0149211 | A1 | 7/2006 | Simpson et al. | |
| 2009/0209933 | A1 * | 8/2009 | Zylberberg ...... | A61B 5/150221 220/592.2 |
| 2009/0227896 | A1 * | 9/2009 | Alvin Tan ............ | A61B 5/1535 600/576 |
| 2012/0323142 | A1 | 12/2012 | Allen et al. | |
| 2014/0012206 | A1 | 1/2014 | Shaw et al. | |
| 2015/0073303 | A1 * | 3/2015 | Shaw .................. | A61M 5/3232 600/576 |
| 2016/0100786 | A1 | 4/2016 | Nishio et al. | |
| 2016/0367177 | A1 | 12/2016 | Edelhauser et al. | |
| 2017/0216835 | A1 | 8/2017 | Ivosevic et al. | |
| 2018/0235529 | A1 | 8/2018 | Allen et al. | |
| 2018/0243515 | A1 * | 8/2018 | Shaw ................. | A61B 5/15003 |

FOREIGN PATENT DOCUMENTS

| | | | | | |
|---|---|---|---|---|---|
| EP | 1579805 | A1 | | 9/2005 | |
| EP | 2617447 | B1 | | 3/2016 | |
| EP | 3018464 | A1 | | 5/2016 | |
| JP | H10188 | A | | 1/1998 | |
| JP | 2002506665 | A | | 3/2002 | |
| JP | 200416297 | A | | 1/2004 | |
| JP | 2005532096 | A | | 10/2005 | |
| JP | 2005328983 | A | | 12/2005 | |
| JP | 200681844 | A | | 3/2006 | |
| JP | 2006110267 | A | | 4/2006 | |
| JP | 2010520036 | A | | 6/2010 | |
| JP | 2013532550 | A | | 8/2013 | |
| JP | 2015187592 | A | | 10/2015 | |
| JP | 2017531782 | A | | 10/2017 | |
| WO | 198103426 | A1 | | 12/1981 | |
| WO | 9947037 | A3 | | 9/1999 | |
| WO | 2004000412 | A1 | | 12/2003 | |
| WO | WO-2006073744 | A2 | * | 7/2006 | ......... A61B 5/15003 |
| WO | 2008109845 | A2 | | 9/2008 | |
| WO | 2012015644 | A8 | | 2/2012 | |
| WO | WO-2012048388 | A1 | * | 4/2012 | ......... A61B 5/14546 |
| WO | WO-2018039307 | A1 | * | 3/2018 | ....... A61B 5/150022 |
| WO | WO-2018111814 | A1 | * | 6/2018 | ............... A61B 5/15 |
| WO | 2018151831 | A1 | | 8/2018 | |

* cited by examiner

ARTERIAL BLOOD GAS COLLECTION SYSTEM

CROSS-REFERENCE TO RELATED APPLICATIONS

This application is the United States national phase of International Application No. PCT/US2019/049680 filed Sep. 5, 2019, and claims priority to U.S. Provisional Application Ser. No. 62/727,869, filed Sep. 6, 2018, entitled "Arterial Blood Gas Collection System", the disclosures of which are hereby incorporated by reference in their entirety.

BACKGROUND OF THE INVENTION

1. Field of the Disclosure

The present disclosure relates generally to arterial blood collection systems.

More particularly, the present disclosure relates to arterial blood collection systems including arterial blood collection elements suitable for radial artery stick and arterial blood modules.

2. Description of the Related Art

Arterial blood collection syringes are used for withdrawing and collecting arterial blood samples from the body of a patient. Once the blood sample is collected, it is subjected to diagnostic analysis for primarily blood gases and often also electrolytes, metabolites, and other elements that are indicative of a condition of a patient. Various types of syringes have been devised for collecting arterial blood samples, which mainly comprise elements from a hypodermic syringe, i.e., a plastic or glass syringe barrel, a sealing elastomeric stopper with or without air vent, and a plunger rod.

Conventional arterial blood collection syringes typically use conventional hypodermic needles with a safety shield that need to be snapped or slid over the needle after a blood collection procedure. Such safety guards are often in the line of sight during a blood collection procedure thereby obscuring a physician's view during this delicate procedure.

Conventional arterial blood collection syringes also have a separate vent cap that requires the needle to be removed before the cap is attached to the syringe to expel trapped air bubbles from a collected sample.

Conventional arterial blood collection syringes that include anticoagulant typically are loaded with the anticoagulant inside the syringe, thus, requiring a user to roll or shake a collected sample to ensure thorough mixing with the anticoagulant.

SUMMARY OF THE INVENTION

The present disclosure provides an arterial blood module removably connectable to an arterial blood collection element. The arterial blood module includes a housing, a needle, a cap removably securable over the needle, a mixing chamber, and a safety shield engaged with a portion of the housing and transitionable from a first shield position in which a portion of the needle is exposed to a second shield position in which the needle is shielded by a portion of the safety shield.

In one embodiment, the present disclosure includes an arterial blood collection system that includes an arterial blood collection element defining a collection chamber and an arterial blood module removably connectable to a portion of the arterial blood collection element.

In an exemplary embodiment, the arterial blood collection system of the present disclosure provides a novel blood collection device for collecting of arterial blood samples using a radial stick technique. The system of the present disclosure provides an efficient system that streamlines and reduces the number of workflow steps and enables single-handed device operation which allows for more efficient Arterial Blood Gas (ABG) collection procedures. The arterial blood module of the present disclosure includes ergonomic touch points, push button safety shield, automatic anticoagulant mixing and integrated vent cap for expelling air bubbles after a collection procedure, if necessary.

In accordance with an embodiment of the present invention, an arterial blood collection system includes an arterial blood collection element defining a collection chamber; and an arterial blood module removably connectable to a portion of the arterial blood collection element, the arterial blood module comprising: a housing having a first end and a second end, a needle extending from the first end, a cap removably securable over the needle; a mixing chamber adjacent the second end, and a safety shield engaged with a portion of the housing and transitionable from a first shield position in which a portion of the needle is exposed to a second shield position in which the needle is shielded by a portion of the safety shield.

In one configuration, the safety shield comprises a shield assembly, and an actuator transitionable from a first actuator position in which the actuator engages a portion of the shield assembly to lock the shield assembly in the first shield position to a second actuator position in which the actuator releases the shield assembly and the safety shield automatically moves to the second shield position. In another configuration, the actuator comprises a push button. In yet another configuration, the shield assembly comprises telescoping shields. In one configuration, the shield assembly comprises a fixed outer shield; a middle movable shield in communication with the fixed outer shield, wherein the middle movable shield moves relative to the fixed outer shield; and an inner movable shield in communication with the middle movable shield, wherein the inner movable shield moves relative to the middle movable shield. In another configuration, with the safety shield in the first shield position, the inner movable shield is nested inside the middle movable shield, and the middle movable shield is nested inside the fixed outer shield. In yet another configuration, with the safety shield in the second shield position, the inner movable shield extends from the middle movable shield, and the middle movable shield extends from the fixed outer shield. In one configuration, the housing of the arterial blood module defines a flow channel from the first end to the second end. In another configuration, the arterial blood module further comprises a sample stabilizer disposed within the flow channel between the first end of the housing and the mixing chamber. In yet another configuration, the arterial blood collection system includes a material including pores disposed within the flow channel between the first end of the housing and the mixing chamber, and a dry anticoagulant powder within the pores of the material. In one configuration, a blood sample dissolves and mixes with the dry anticoagulant powder while passing through the material. In another configuration, the material is an open cell foam. In yet another configuration, the sample stabilizer is the dry anticoagulant powder. In one configuration, the housing of the arterial blood module defines a vent chamber. In another configuration, the arterial blood module further comprises a venting plug that allows air to pass therethrough and prevents a blood sample from passing therethrough, wherein a portion of the venting plug is in communication with the vent chamber. In yet another configuration, the arterial blood module further comprises a first valve, and wherein, with the arterial blood module connected to the arterial blood collection element, the blood sample enters the collection chamber of the arterial blood collection element via the needle and the first valve. In one configuration, the first valve allows the blood sample to pass from the arterial blood module to the collection chamber of the arterial blood collection element. In another configuration, the first valve blocks the blood sample from passing from the collection chamber of the arterial blood collection element back to the arterial blood module. In yet another configuration, the arterial blood module further comprises a second valve, and wherein, with the arterial blood module connected to the arterial blood collection element, air contained in the collection chamber of the arterial blood collection element and a portion of the blood sample enter the vent chamber via the second valve. In one configuration, the air travels out of the arterial blood module via the venting plug. In another configuration, the arterial blood module includes a first finger grip portion. In yet another configuration, the arterial blood module includes a second finger grip portion, wherein the first finger grip portion is opposite the second finger grip portion. In one configuration, the needle comprises thin wall needle technology. In another configuration, the arterial blood collection element includes a plunger rod assembly including a stopper and a plunger rod.

In accordance with another embodiment of the present invention, an arterial blood module includes a housing having a first end and a second end; a needle extending from the first end; a cap removably securable over the needle; a mixing chamber adjacent the second end; and a safety shield engaged with a portion of the housing and transitionable from a first shield position in which a portion of the needle is exposed to a second shield position in which the needle is shielded by a portion of the safety shield.

In one configuration, the arterial blood module is removably connectable to a portion of an arterial blood collection element. In another configuration, the arterial blood collection element defines a collection chamber.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
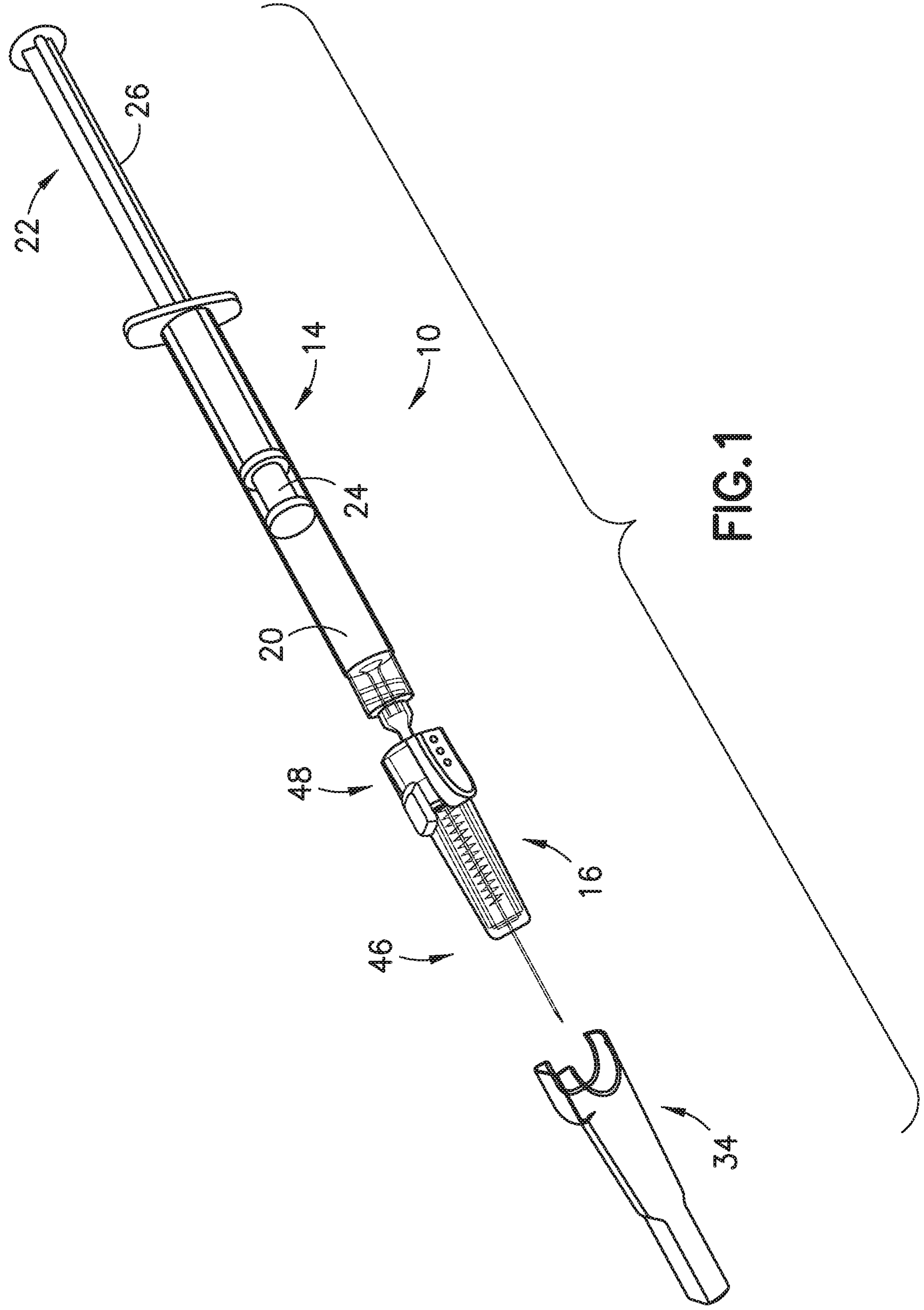
FIG. 1 is a perspective view of an arterial blood collection system in accordance with an embodiment of the present invention.
Figure 2:
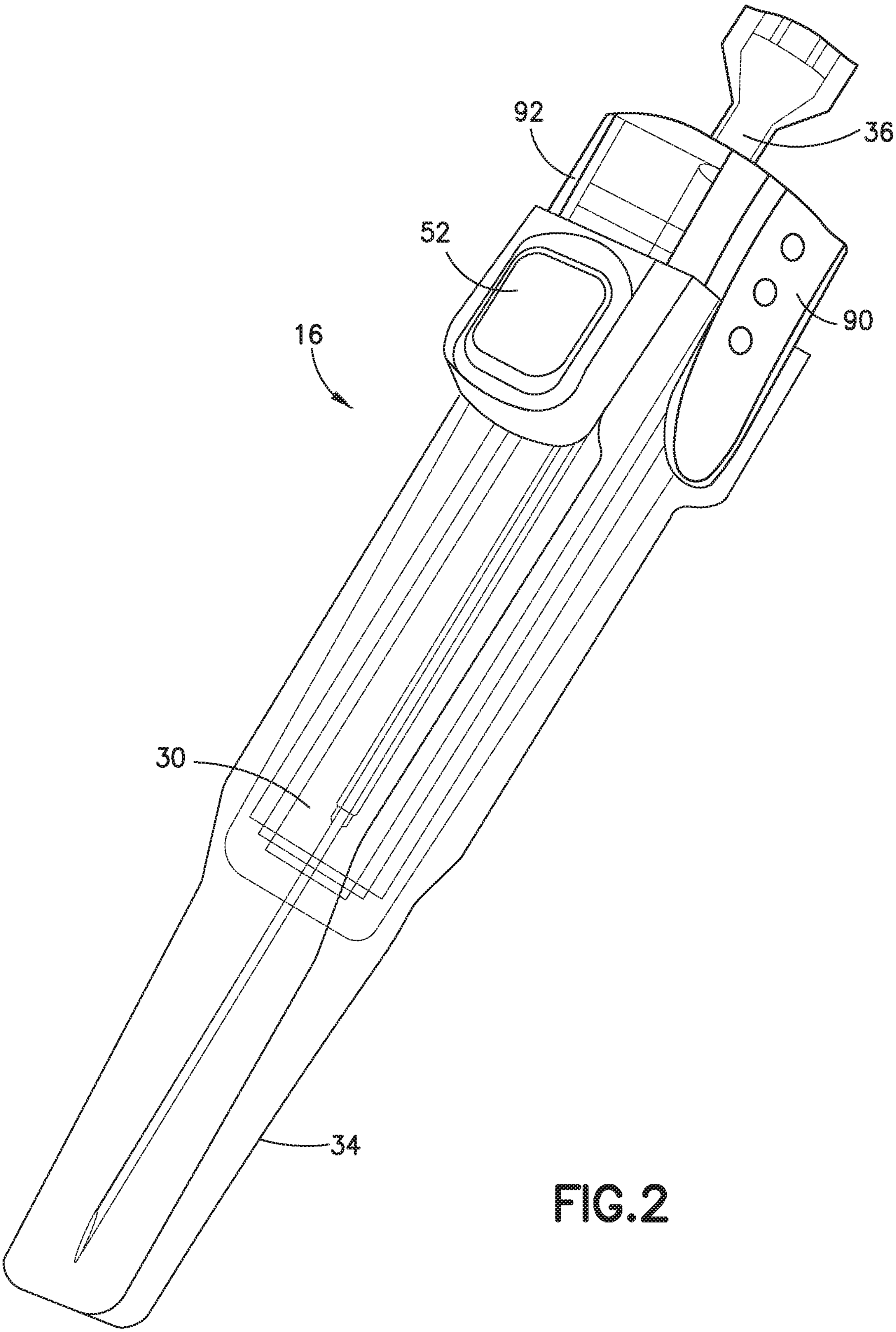
FIG. 2 is a perspective view of an arterial blood module with a cap secured over a needle in accordance with an embodiment of the present invention.
Figure 3:
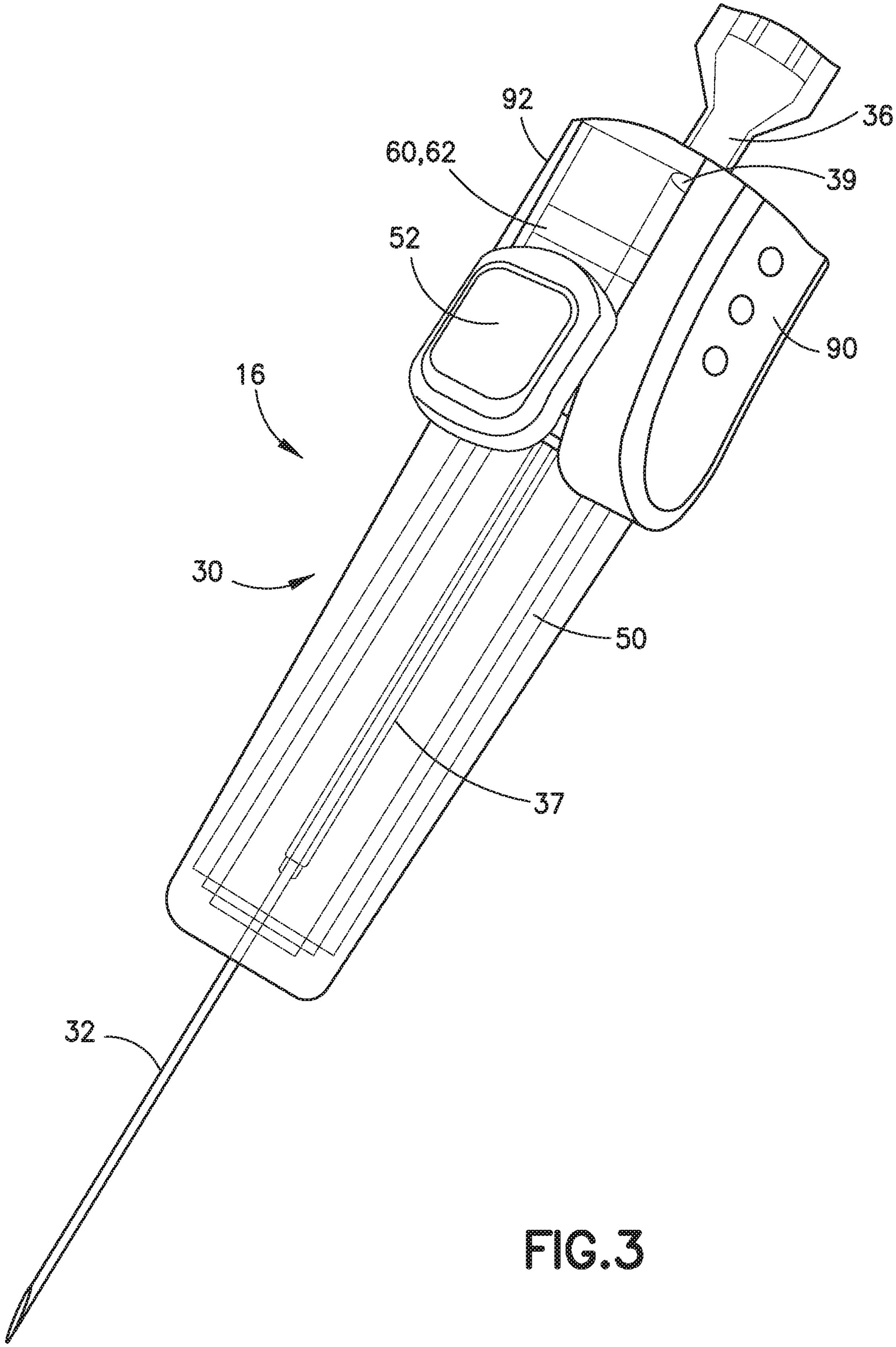
FIG. 3 is a perspective view of an arterial blood module with a cap removed from a needle in accordance with an embodiment of the present invention.
Figure 4:
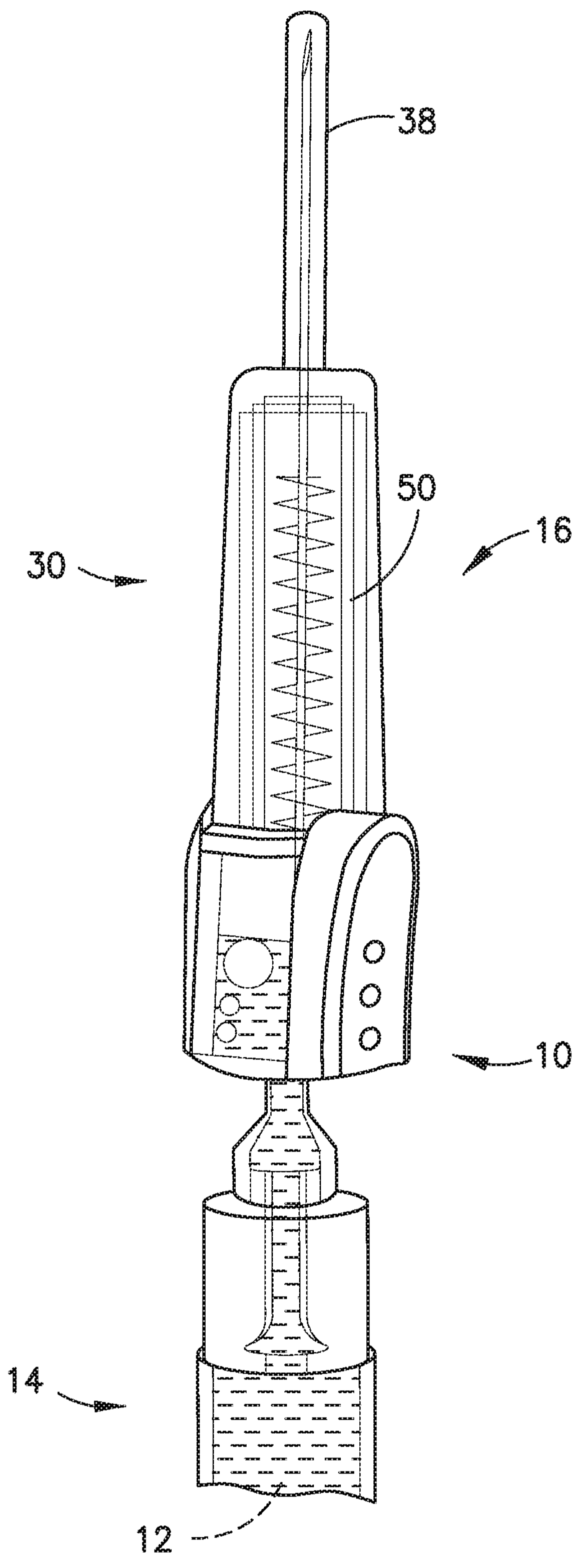
FIG. 4 is a perspective view of an arterial blood collection system with air bubbles being expelled from the system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present disclosure provides an arterial blood module removably connectable to an arterial blood collection element. The arterial blood module includes a housing, a needle, a cap removably securable over the needle, a mixing chamber, and a safety shield engaged with a portion of the housing and transitionable from a first shield position in which a portion of the needle is exposed to a second shield position in which the needle is shielded by a portion of the safety shield. In one embodiment, the present disclosure includes an arterial blood collection system that includes an arterial blood collection element defining a collection chamber and an arterial blood module removably connectable to a portion of the arterial blood collection element.

In an exemplary embodiment, the arterial blood collection system of the present disclosure provides a novel blood collection device for collecting of arterial blood samples using a radial stick technique. The system of the present disclosure provides an efficient system that streamlines and reduces the number of workflow steps and enables single-handed device operation which allows for more efficient Arterial Blood Gas (ABG) collection procedures. The arterial blood module of the present disclosure includes ergonomic touch points, push button safety shield, automatic anticoagulant mixing and integrated vent cap for expelling air bubbles after a collection procedure, if necessary.

FIGS. 1-20 illustrate exemplary embodiments of an arterial blood collection system 10 of the present disclosure that is adapted to receive a biological fluid sample, such as an arterial blood sample 12. In one embodiment, the arterial blood collection system 10 of the present disclosure includes an arterial blood collection element 14 and an arterial blood module 16 that is removably connectable to a portion of the arterial blood collection element 14.

Referring to FIGS. 1 and 4-12, in one embodiment, the arterial blood collection element 14 of the present disclosure is adapted to receive a biological fluid sample, such as an arterial blood sample 12, and defines a collection chamber 20. In an exemplary embodiment, the arterial blood collection element 14 includes a plunger rod assembly 22 having a stopper 24 and a plunger rod 26. In one embodiment, the arterial blood collection element 14 is a conventional arterial blood gas syringe assembly, e.g., either a luer-lock or luer-slip arterial blood gas syringe assembly. The arterial blood module 16 of the present disclosure may be compatible with any conventional arterial blood collection elements or arterial blood gas syringe assemblies.

When using a system 10 of the present disclosure to remove arterial blood, the blood at arterial pressure is greater than the normal atmospheric or ambient pressure within the collection chamber 20 of the arterial blood collection element 14, and thus, upon inserting a needle 32 of the arterial blood module 16 into an artery, an arterial blood sample 12 will flow from the patient through the arterial blood module 16 to the collection chamber 20 of the arterial blood collection element 14, as described in more detail below. In this manner, the system 10 of the present disclosure self-fills due to the arterial blood pressure and a vented arterial blood gas syringe stopper.

Referring to FIGS. 1-20, in one embodiment, the arterial blood module 16 of the present disclosure is removably connectable to a portion of the arterial blood collection element 14 and includes a housing 30, a needle 32, a cap 34, a mixing chamber 36, a flow channel 37, a safety shield 38, and a sample stabilizer 39. In one embodiment, the housing 30 includes a first end 46 and a second end 48. In one embodiment, the housing 30 of the arterial blood module 16 defines a flow channel 37 that extends from the first end 46 to the second end 48.

In an exemplary embodiment, the arterial blood module 16 of the present disclosure is removably connectable to a portion of the arterial blood collection element 14 via conventional methods and structure. For example, in one embodiment, the arterial blood module 16 of the present disclosure is removably connectable to a portion of the arterial blood collection element 14 via a standard luer connection.

Advantageously, the arterial blood module 16 of the present disclosure allows for automatic mixing with a sample stabilizer 39. For example, in one embodiment, the mixing chamber 36 is provided in fluid communication with the flow channel 37. The mixing chamber 36 and the sample stabilizer 39 are positioned such that a biological fluid sample, such as an arterial blood sample 12, will first pass through a sample stabilizer 39, then the blood sample 12 and the sample stabilizer 39 pass through the mixing chamber 36, and subsequently the sample 12 with the sample stabilizer 39 properly mixed therein flow into the collection chamber 20 of the arterial blood collection element 14. In this way, the blood sample 12 may be mixed with a sample stabilizer 39, such as an anticoagulant or other additive, provided within the arterial blood module 16, before passing through the mixing chamber 36 for proper mixing of the sample stabilizer 39 within the blood sample 12, and then the stabilized sample is received and stored within the collection chamber 20 of the arterial blood collection element 14.

In one embodiment, a sample stabilizer 39 is disposed within the flow channel 37 between the first end 46 of the housing 30 and the mixing chamber 36. The arterial blood module 16 of the present disclosure provides passive and fast mixing of a blood sample 12 with the sample stabilizer 39. For example, the arterial blood module 16 includes a mixing chamber 36 that allows for passive mixing of the blood sample 12 with an anticoagulant or another additive, such as a blood stabilizer, as the blood sample 12 flows through the mixing chamber 36.

The sample stabilizer can be an anticoagulant, or a substance designed to preserve a specific element within the blood such as, for example, RNA, protein analyte, or other element. In one embodiment, the sample stabilizer 39 is disposed within the flow channel 37 between the first end 46 of the housing 30 and the mixing chamber 36. In other embodiments, the sample stabilizer 39 may be disposed in other areas within the housing 30 of the arterial blood module 16.

Figure 19:
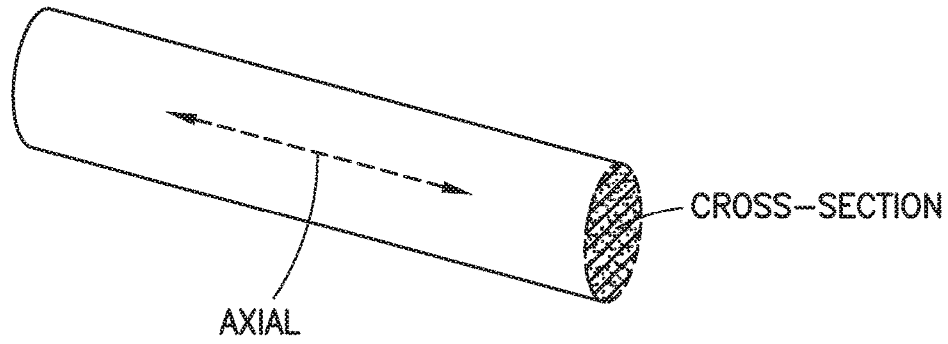
FIG. 19 is a perspective view of an open cell foam material in accordance with an embodiment of the present invention.
Figure 20:
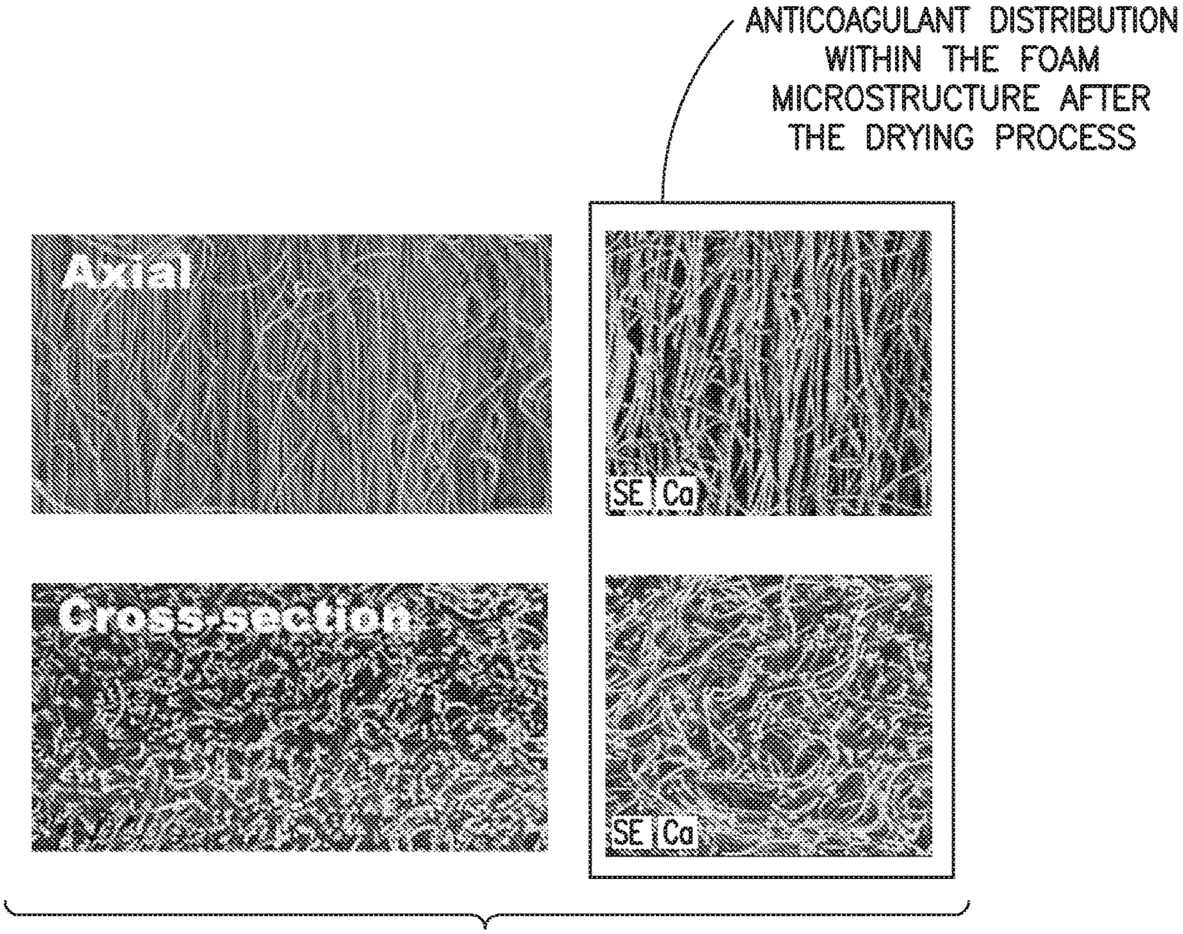
FIG. 20 is a microscopic view of the microstructure of an open cell foam material having a dry anticoagulant powder distributed throughout its microstructure in accordance with an embodiment of the present invention.

Referring to FIGS. 19-20, in one embodiment, the arterial blood module 16 includes a material 40 including pores 42 that is disposed within the flow channel 37 between the first end 46 of the housing 30 and the mixing chamber 36 and a dry anticoagulant powder 44 that is within the pores 42 of the material 40. In this manner, the arterial blood module 16 may include a dry anticoagulant, such as Heparin or EDTA, deposited on or within a portion of the arterial blood module 16. In one embodiment, the material 40 is an open cell foam that contains dry anticoagulant dispersed within the cells of the open cell foam to promote the effectiveness of the flow-through mixing and anticoagulant uptake. In one embodiment, the sample stabilizer 39 is the dry anticoagulant powder 44.

In one embodiment, the open cell foam may be treated with an anticoagulant to form a dry anticoagulant powder finely distributed throughout the pores of the open cell foam. As the blood sample 12 enters the arterial blood module 16, the blood sample 12 passes through the open cell foam and is exposed to the anticoagulant powder available throughout the internal pore structure of the open cell foam. In this manner, the sample 12 dissolves and mixes with the dry anticoagulant powder 44 while passing through the material 40 or open cell foam.

The open cell foam may be a soft deformable open cell foam that is inert to blood, for example, a melamine foam, such as Basotect® foam commercially available from BASF, or may consist of a formaldehyde-melamine-sodium bisulfite copolymer. The open cell foam may also be a flexible, hydrophilic open cell foam that is substantially resistant to heat and organic solvents. In one embodiment, the foam may include a sponge material.

The anticoagulant or other additive may be introduced into the open cell foam by soaking the foam in a liquid solution of the additive and water and subsequently evaporating the water forming a dry additive powder finely distributed throughout the internal structure of the foam.

The arterial blood module 16 includes a mixing chamber 36 that allows for passive mixing of the blood sample 12 with an anticoagulant or another additive, such as a blood stabilizer, as the blood sample 12 flows through the mixing chamber 36. In one embodiment, the mixing chamber 36 is disposed between the first end 46 and the second end 48 of the housing 30 of the arterial blood module 16. In one embodiment, the mixing chamber 36 is adjacent the second end 48.

The internal portion of the mixing chamber 36 may have any suitable structure or form as long as it provides for the mixing of the blood sample 12 with an anticoagulant or another additive as the blood sample 12 passes through the flow channel 37 of the arterial blood module 16.

The mixing chamber 36 receives the sample 12 and the sample stabilizer 39 therein and effectuates distributed mixing of the sample stabilizer 39 within the sample 12. The mixing chamber 36 effectuates distributed mixing of the sample stabilizer 39 within the sample 12 and prevents a very high sample stabilizer concentration in any portion of the blood sample 12. This prevents underdosing of the sample stabilizer 39 in any portion of the blood sample 12. The mixing chamber 36 effectuates distributed mixing of the sample stabilizer 39 within the sample 12 so that an approximately equal amount and/or concentration of the sample stabilizer 39 is dissolved throughout the blood sample 12, e.g., an approximately equal amount and/or concentration of the sample stabilizer 39 is dissolved into the blood sample 12 from a front portion of the blood sample 12 to a rear portion of the blood sample 12.

Referring to FIGS. 1-20, in one embodiment, the arterial blood module 16 includes a needle 32 extending from the first end 46 of the housing 30. In an exemplary embodiment, the needle 32 includes thin wall needle technology. For example, the thin wall needle technology of the present disclosure provides a small gage needle while still maintaining a high flow rate resulting in a fast fill time and shorter patient exposure to an uncomfortable procedure.

Referring to FIGS. 1-20, in one embodiment, the arterial blood module 16 includes a safety cap 34 that is removably securable over the needle 32. The safety cap 34 ensures the needle 32 is completely covered and shielded before any collection procedure begins. Before use of the arterial blood module 16, a user can remove the safety cap 34 from the arterial blood module 16.

Referring to FIGS. 1-20, in one embodiment, the arterial blood module 16 includes a safety shield 38 that is engaged with a portion of the housing 30 and is transitionable from a first shield position (FIG. 3) in which a portion of the needle 32 is exposed to a second shield position (FIGS. 14, 16, and 18) in which the needle 32 is shielded by a portion of the safety shield 38.

Figure 16:
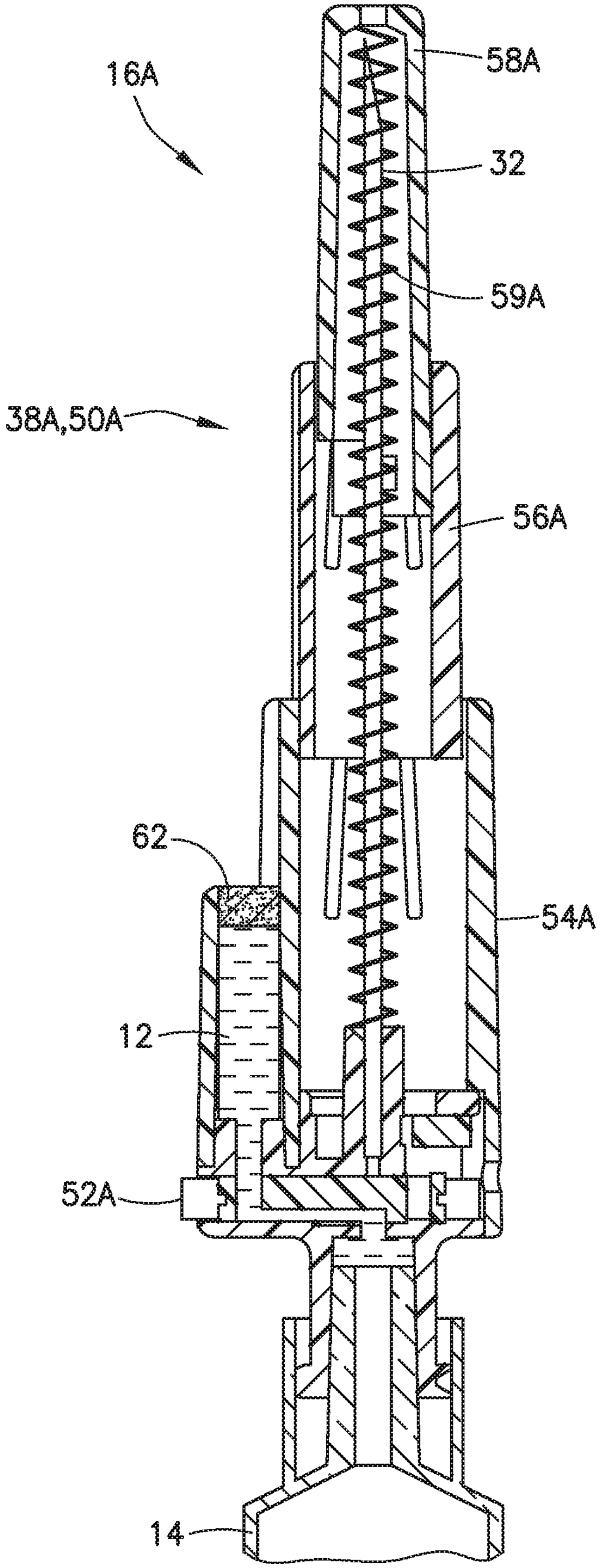
FIG. 16 is a cross-sectional view of a portion of an arterial blood module with a safety shield in a second shield position in accordance with another embodiment of the present invention.
Figure 17:
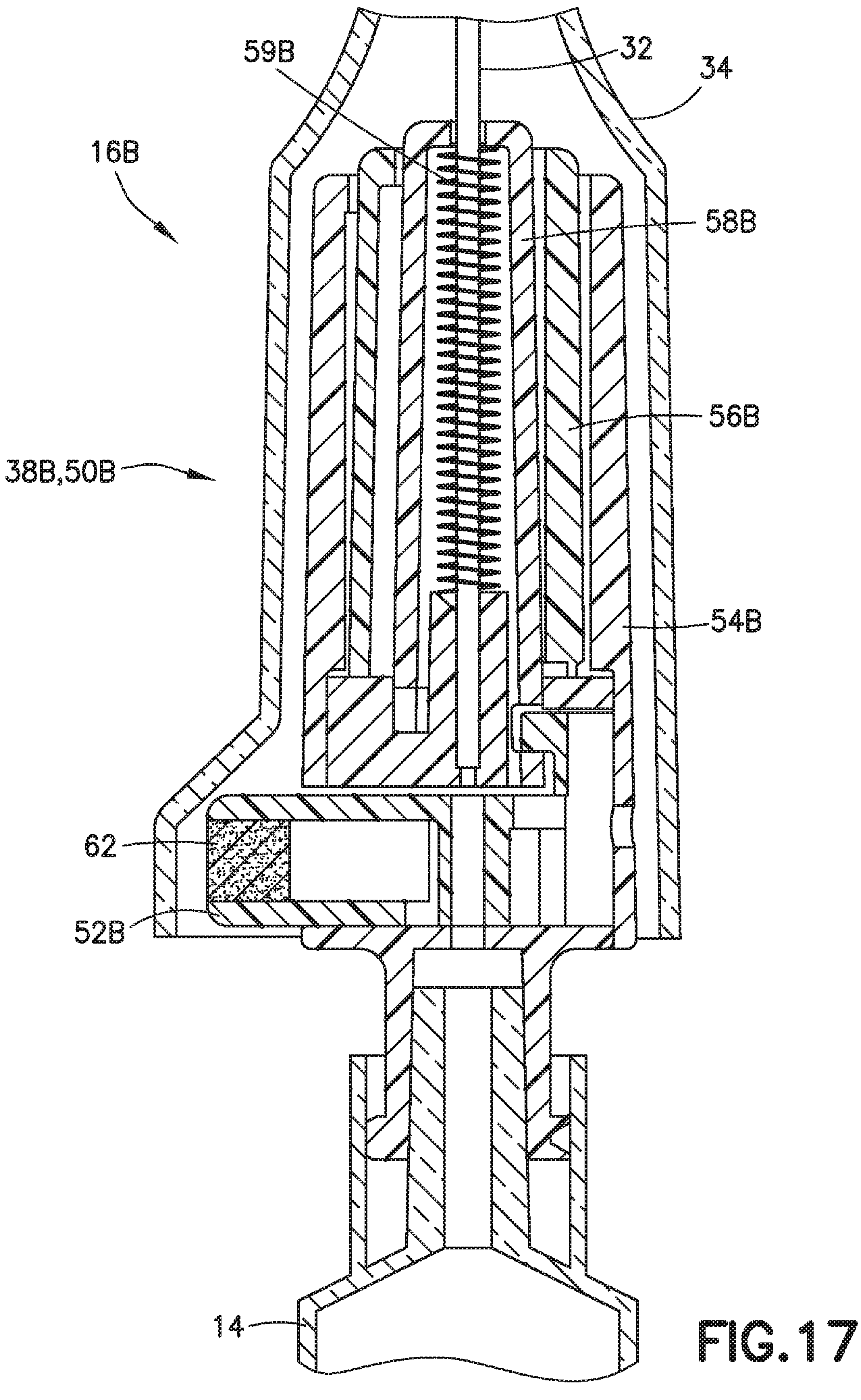
FIG. 17 is a cross-sectional view of a portion of an arterial blood module with a safety shield in a first shield position in accordance with another embodiment of the present invention.
Figure 18:
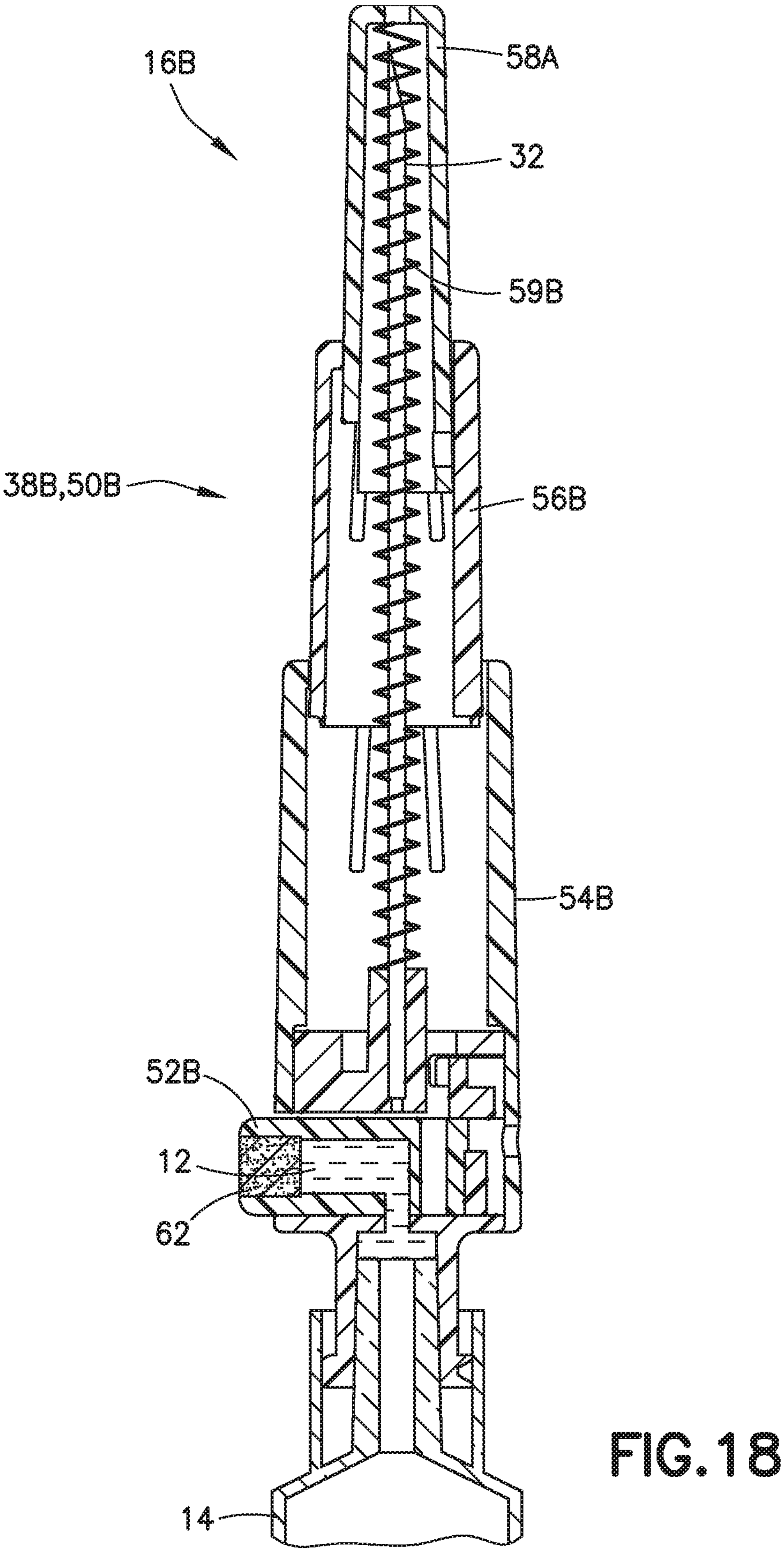
FIG. 18 is a cross-sectional view of a portion of an arterial blood module with a safety shield in a second shield position in accordance with another embodiment of the present invention.

Advantageously, the safety shield 38 of the arterial blood module 16 of the present disclosure allows for automatic shielding of the needle 32 after use. For example, in one exemplary embodiment, the safety shield 38 includes a shield assembly 50 and an actuator 52 that is transitionable from a first actuator position (FIGS. 13, 15, and 17) in which the actuator 52 engages a portion of the shield assembly 50 to lock the shield assembly 50 in the first shield position (FIG. 3) to a second actuator position (FIGS. 14, 16, and 18) in which the actuator 52 releases the shield assembly 50 and the safety shield 38 automatically moves to the second shield position (FIGS. 14, 16, and 18). In one exemplary embodiment, the actuator 52 comprises a push button. In this manner, an integrated push-button safety shield 38 of the present disclosure provides a device that can be single-handed activated by the simple push of a button after the collection procedure is complete while not obscuring a healthcare worker's view during the procedure. In this way, the safety shield 38 of the arterial blood module 16 of the present disclosure allows for automatic shielding of the needle 32 after use. For example, in one exemplary embodiment, upon activating the actuator 52 of the safety shield 38, a spring 59 exerts a force on a portion of the shield assembly 50 to automatically move the safety shield 38 to the second shield position in which the needle 32 is shielded by a portion of the safety shield 38.

Referring to FIGS. 13-18, in exemplary embodiments, the shield assembly 50 includes telescoping shields. For example, referring to FIGS. 13-14, in one exemplary embodiment, the shield assembly 50 includes a fixed outer shield 54; a middle movable shield 56 in communication with the fixed outer shield 54, wherein the middle movable shield 56 moves relative to the fixed outer shield 54; and an inner movable shield 58 in communication with the middle movable shield 56, wherein the inner movable shield 58 moves relative to the middle movable shield 56.

Figure 13:
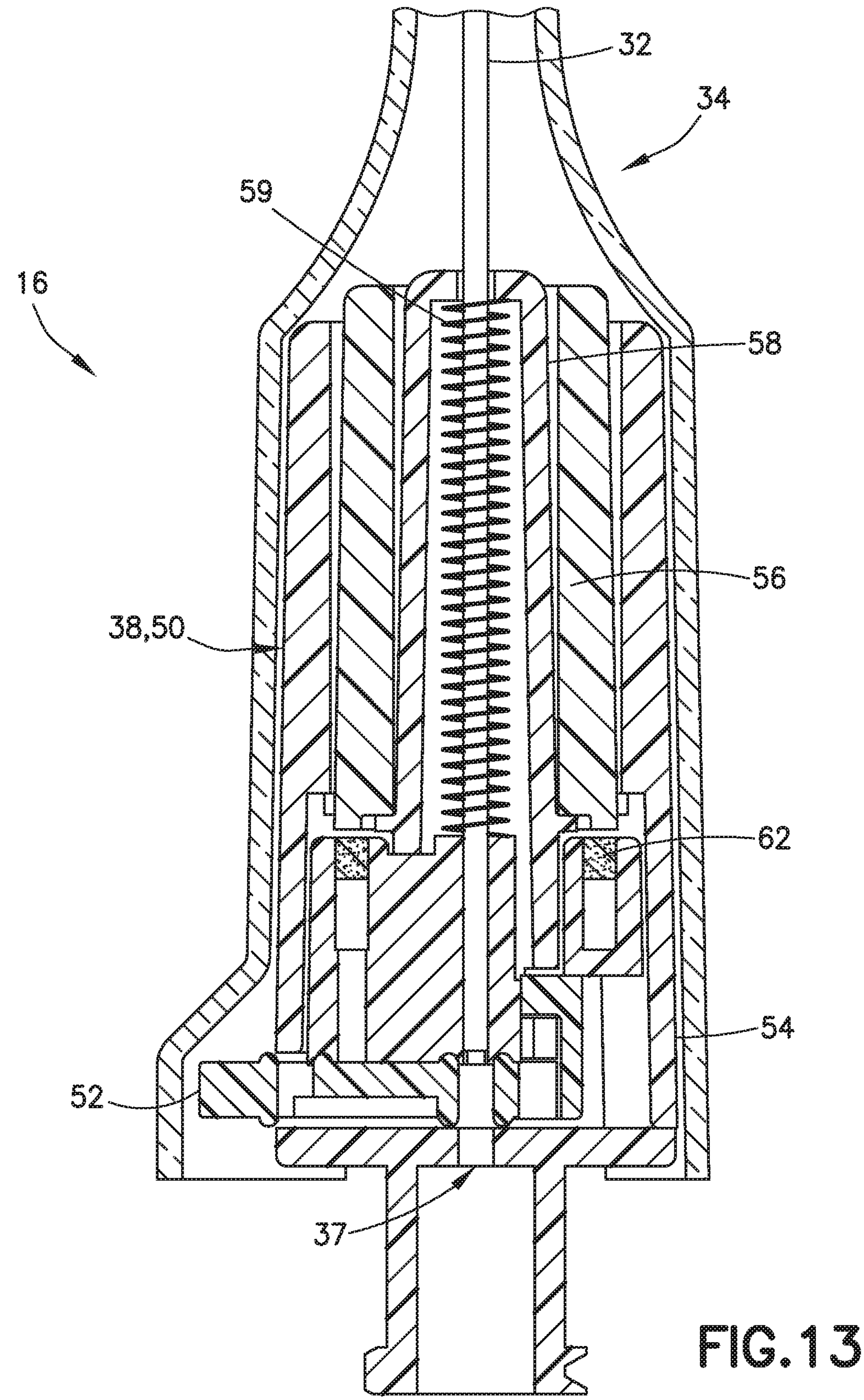
FIG. 13 is a cross-sectional view of a portion of an arterial blood module with a safety shield in a first shield position in accordance with an embodiment of the present invention.
Figure 14:
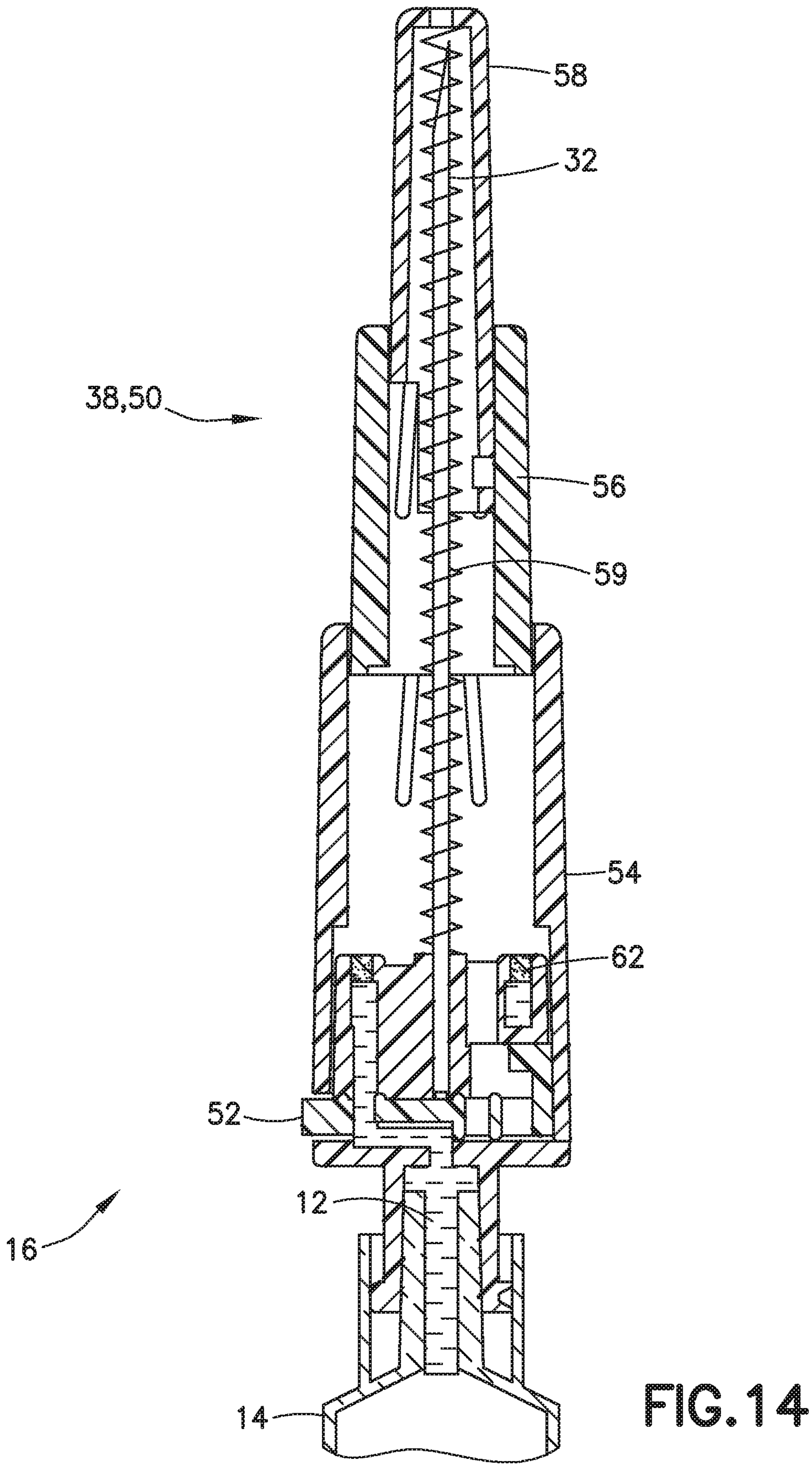
FIG. 14 is a cross-sectional view of a portion of an arterial blood module with a safety shield in a second shield position in accordance with an embodiment of the present invention.
Figure 15:
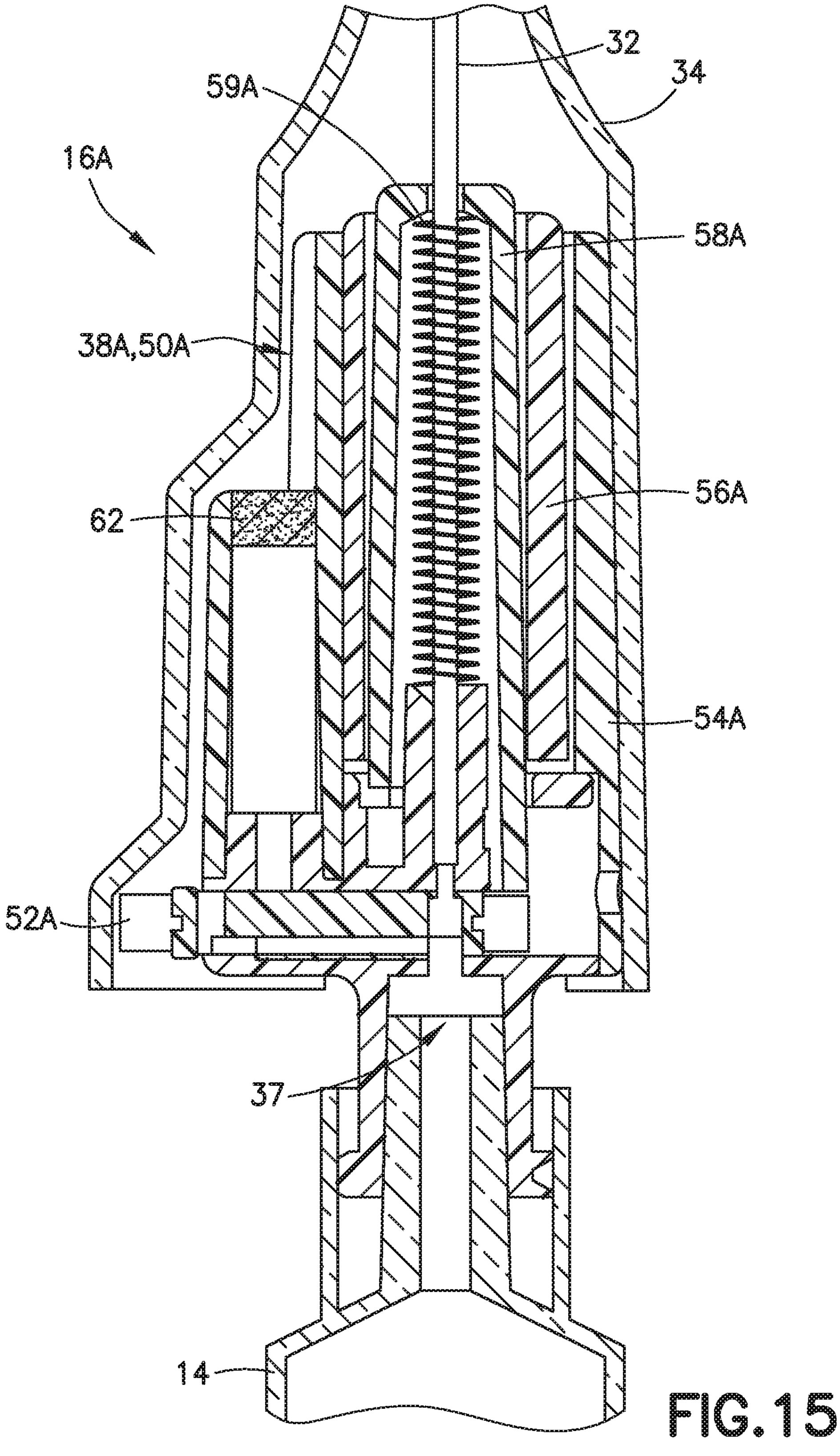
FIG. 15 is a cross-sectional view of a portion of an arterial blood module with a safety shield in a first shield position in accordance with another embodiment of the present invention.

Referring to FIG. 13, in one embodiment, with the safety shield 38 in the first shield position, the inner movable shield 58 is nested inside the middle movable shield 56, and the middle movable shield 56 is nested inside the fixed outer shield 54.

Referring to FIG. 14, in one embodiment, with the safety shield 38 in the second shield position, the inner movable shield 58 extends from the middle movable shield 56, and the middle movable shield 56 extends from the fixed outer shield 54.

In one exemplary embodiment, upon activating the actuator 52 of the safety shield 38, a spring 59 exerts a force on a portion of the shield assembly 50 to automatically move the safety shield 38 to the second shield position in which the needle 32 is shielded by a portion of the safety shield 38.

For example, referring to FIG. 13, in a first position, the spring 59 is disposed within the inner shield 58 in a compressed position. Referring to FIG. 14, upon activating the actuator 52 of the safety shield 38, the spring 59 is able to exert the stored force on a portion of the inner shield 58 to automatically move the telescoping shields 54, 56, 58 to the second shield position in which the needle 32 is shielded by a portion of the shield assembly 50.

FIGS. 15-18 illustrate other exemplary embodiments. The embodiment illustrated in FIGS. 15-16 includes similar components to the embodiment illustrated in FIGS. 13-14, and the similar components are denoted by a reference number followed by the letter A. The embodiment illustrated in FIGS. 17-18 also includes similar components to the embodiment illustrated in FIGS. 13-14, and the similar components are denoted by a reference number followed by the letter B. For the sake of brevity, these similar components and the similar steps of using arterial blood module 16A (FIGS. 15-16) and arterial blood module 16B (FIGS. 17-18) will not all be discussed in conjunction with the embodiments illustrated in FIGS. 15-16 and FIGS. 17-18.

Advantageously, the arterial blood module 16 of the present disclosure allows for an integrated air venting system which allows for the removal of trapped air bubbles by simply expelling it into a vented compartment inside the arterial blood module 16. For example, in one exemplary embodiment, the arterial blood module 16 includes a vent chamber 60, a venting plug 62, a first valve 64, and a second valve 66.

In one embodiment, the housing 30 of the arterial blood module 16 defines a vent chamber 60. In an exemplary embodiment, the arterial blood module 16 includes a venting plug 62 that allows air to pass therethrough and prevents a blood sample 12 from passing therethrough, wherein a portion of the venting plug 62 is in communication with the vent chamber 60. In this manner, any air bubbles contained within the arterial blood collection element 14 can be expelled outside of the system 10 through the vent chamber 60 and out the venting plug 62. The construction of the arterial blood module 16, the vent chamber 60, and the venting plug 62 allows air to pass through the arterial blood module 16 while preventing the blood sample 12 from passing through the arterial blood module 16 and may include a hydrophobic filter.

Figure 12:
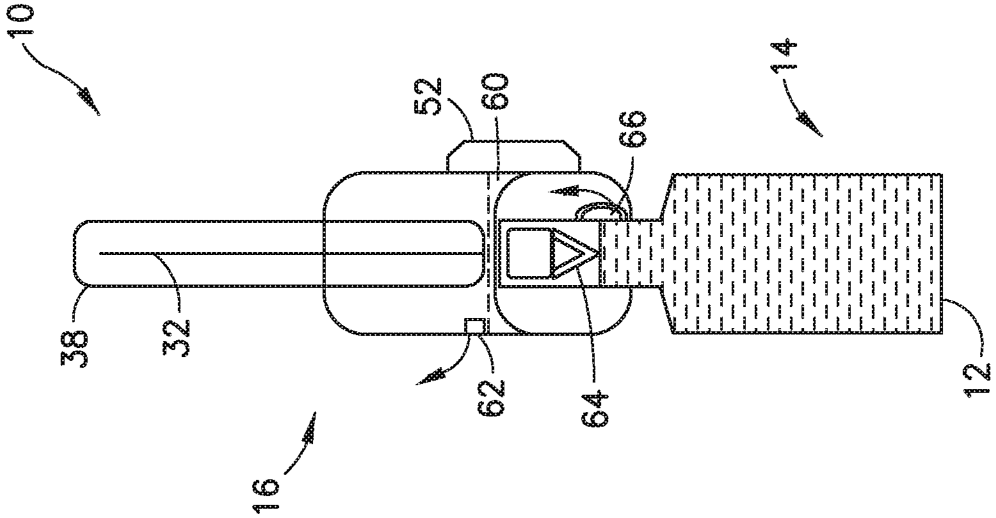
FIG. 12 is a third schematic view of an arterial blood collection system in accordance with an embodiment of the present invention.
Figure 11:
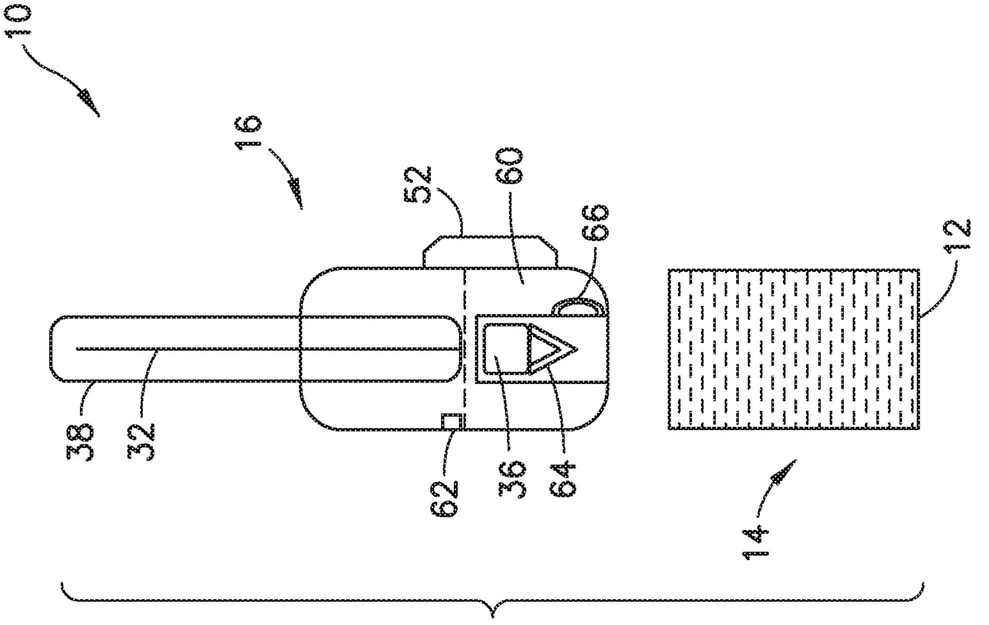
FIG. 11 is a second schematic view of an arterial blood collection system in accordance with an embodiment of the present invention.
Figure 10:
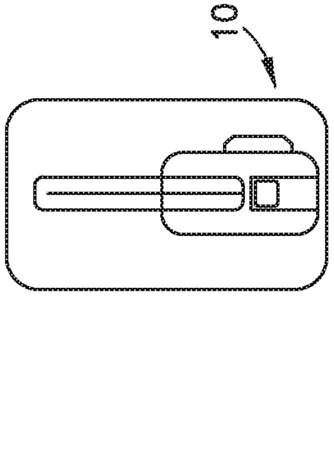
FIG. 10 is a first schematic view of an arterial blood collection system in accordance with an embodiment of the present invention.

Referring to FIGS. 10-12, in one embodiment, the arterial blood module 16 includes a first valve 64. In an exemplary embodiment, with the arterial blood module 16 connected to the arterial blood collection element 14, the blood sample 12 enters the collection chamber 20 of the arterial blood collection element 14 via the needle 32 and the first valve 64. The first valve 64 allows the blood sample 12 to pass from the arterial blood module 16 to the collection chamber 20 of the arterial blood collection element 14. The first valve 64 blocks the blood sample 12 from passing from the collection chamber 20 of the arterial blood collection element 14 back to the arterial blood module 16. In one embodiment, the first valve 64 is a one-way valve.

In one embodiment, the arterial blood module 16 includes a second valve 66. In an exemplary embodiment, with the arterial blood module 16 connected to the arterial blood collection element 14, air contained in the collection chamber 20 of the arterial blood collection element 14 and a portion of the blood sample 12 enter the vent chamber 60 via the second valve 66. In one embodiment, the second valve 66 is a one-way valve.

Advantageously, the arterial blood module 16 of the present disclosure provides an ergonomic design with designated touch points to facilitate precise and easy handling of the arterial blood module 16 during a collection procedure. For example, in one exemplary embodiment, referring to FIGS. 1-20, the arterial blood module 16 includes a first finger grip portion 90. In another exemplary embodiment, the arterial blood module 16 includes a second finger grip portion 92, wherein the first finger grip portion 90 is disposed opposite the second finger grip portion 92.

Referring to FIGS. 5-9, use of an arterial blood collection system 10 of the present disclosure having an arterial blood module 16 and an arterial blood collection element 14 will now be described.

Figure 5:
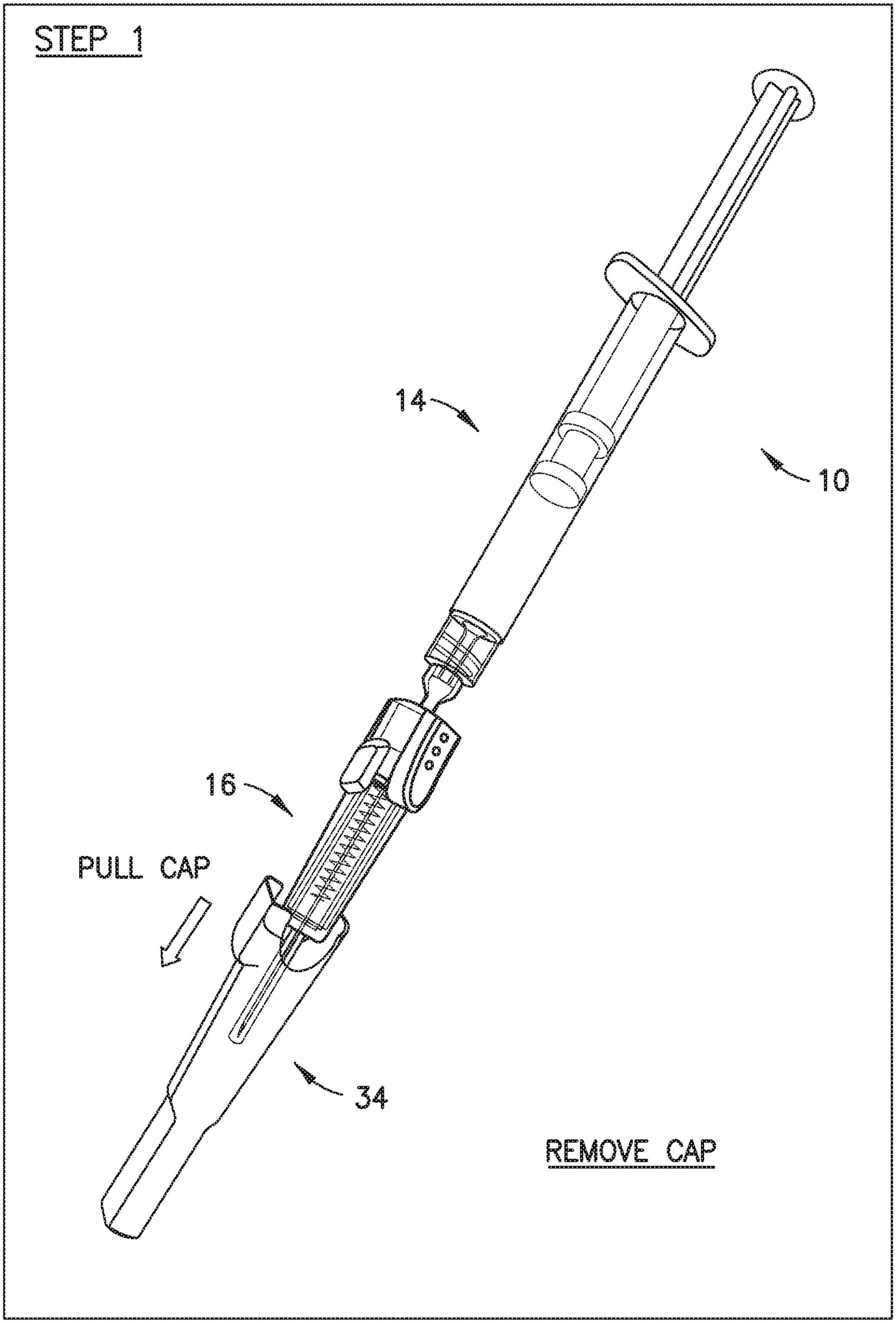
FIG. 5 is a perspective view of a first step of using a system of the present disclosure in accordance with an embodiment of the present invention.

Referring to FIG. 5, a safety cap 34 ensures that the needle 32 of the arterial blood module 16 is completely covered and shielded before any collection procedure begins. Before use of the arterial blood module 16, a user can remove the safety cap 34 by pulling it away from the arterial blood module 16 as shown in FIG. 5.

Figure 6:
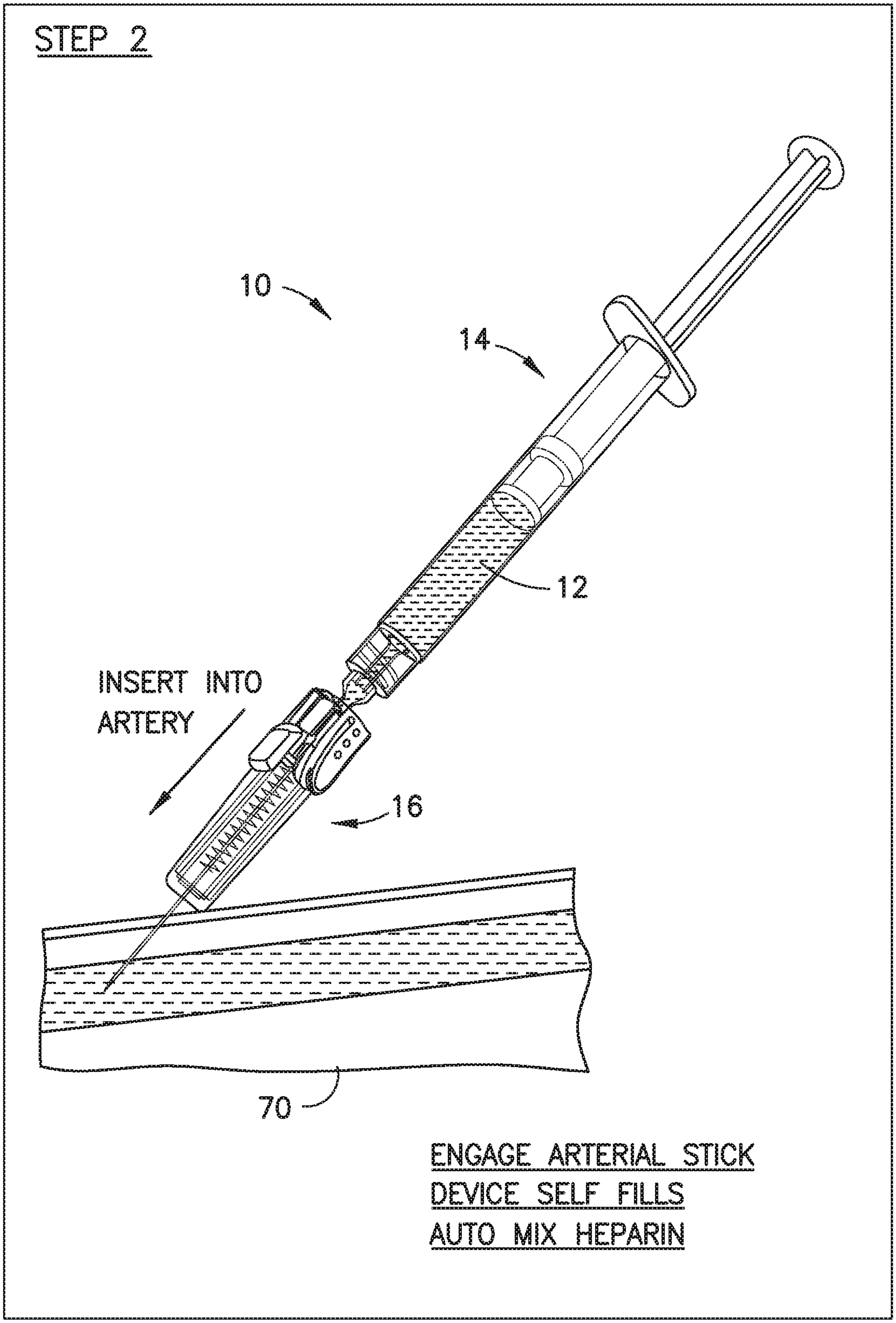
FIG. 6 is a perspective view of a second step of using a system of the present disclosure in accordance with an embodiment of the present invention.

Referring to FIG. 6, the needle 32 of the system 10 is inserted into an artery 70 of a patient. The arterial blood collection element 14 of the arterial blood collection system 10 self-fills due to the arterial blood pressure and vented arterial blood gas syringe stopper as described above. An arterial blood sample 12 is automatically mixed with a sample stabilizer 39, as described above, as the blood sample 12 automatically travels from the artery 70 of the patient to the collection chamber 20 of the arterial blood collection element 14 via the arterial blood module 16.

Figure 7:
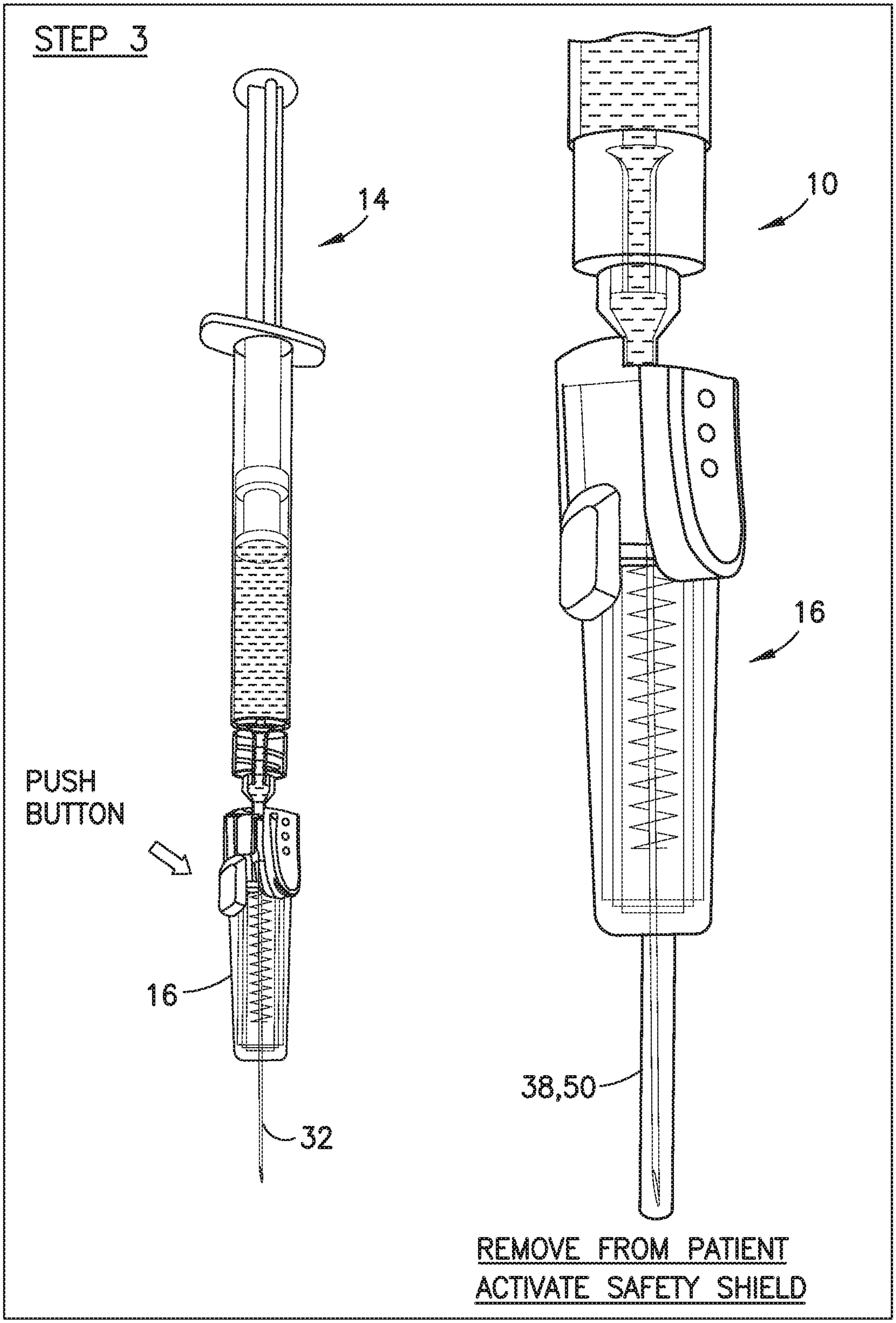
FIG. 7 is a perspective view of a third step of using a system of the present disclosure in accordance with an embodiment of the present invention.

Referring to FIG. 7, the needle 32 is then removed from the artery 70 of the patient and the safely shield 38 is activated by pressing the actuator 52 which automatically shields the needle 32 with the safety shield 38. In this manner, the safety shield 38 is locked into a shielded position safely covering the needle 32 for safe handling and disposal of the arterial blood module 16.

Figure 8:
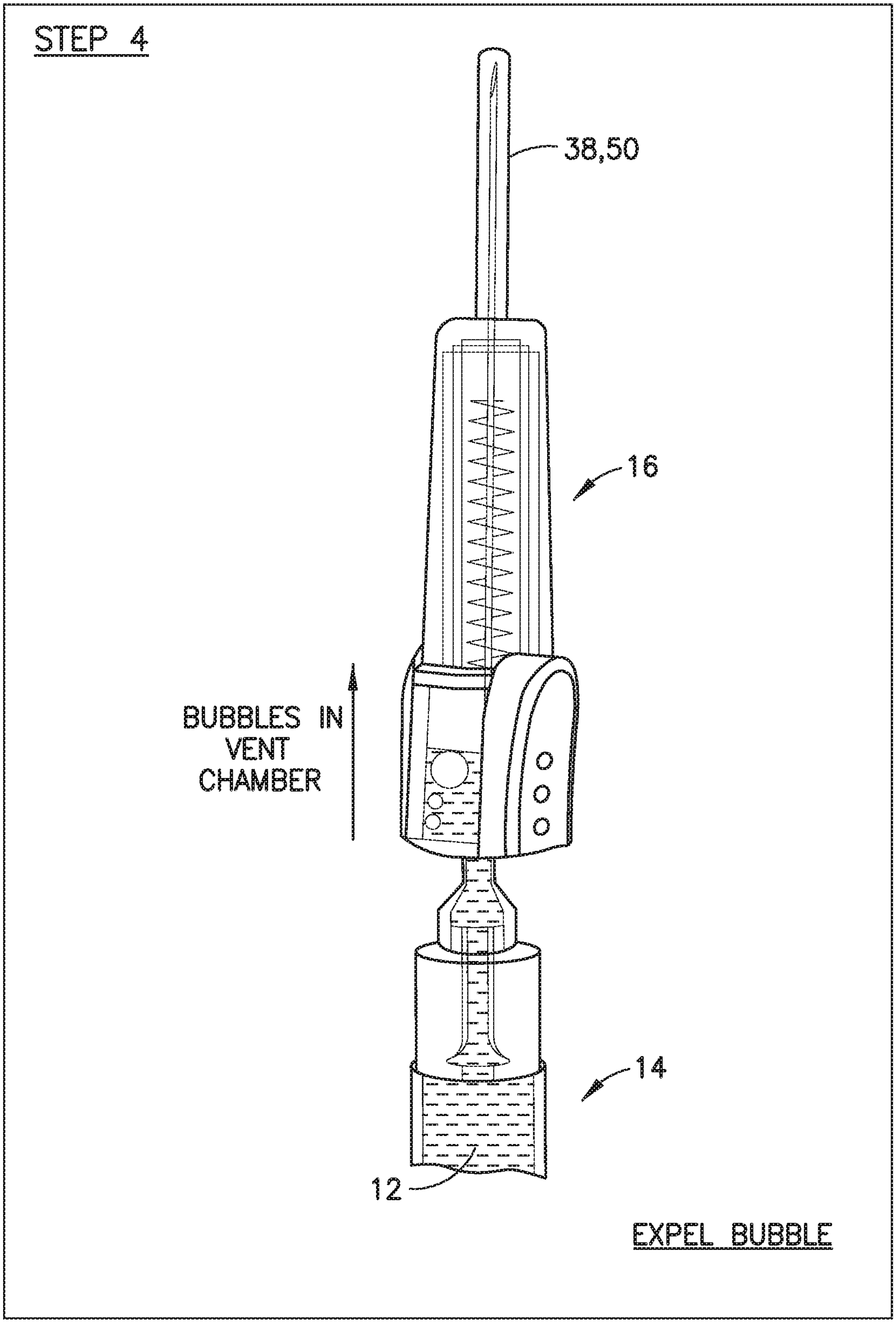
FIG. 8 is a perspective view of a fourth step of using a system of the present disclosure in accordance with an embodiment of the present invention.

Referring to FIG. 8, the arterial blood collection system 10 is then orientated vertically by pointing the safely shielded needle 32 in an upward configuration. Next, a user can push the plunger rod 26 of the arterial blood collection element 14 to expel any trapped air bubbles from the collection chamber 20 of the arterial blood collection element 14 and out the arterial blood module 16 via the vent chamber 60 and the venting plug 62, as described in detail above.

Figure 9:
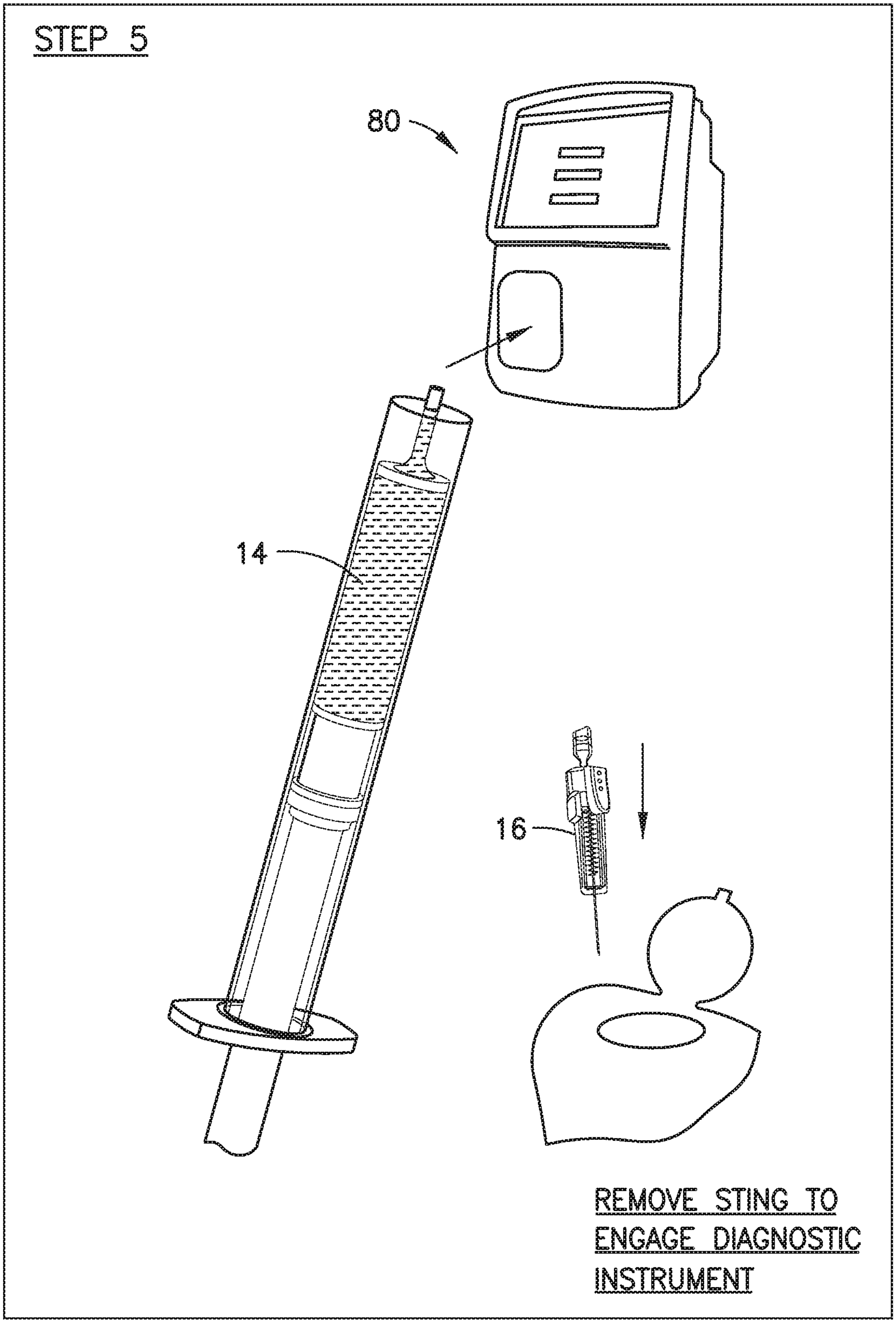
FIG. 9 is a perspective view of a fifth step of using a system of the present disclosure in accordance with an embodiment of the present invention.

Referring to FIG. 9, the arterial blood module 16 is then removed from the arterial blood collection element 14. In this manner, the arterial blood module 16 can be safely disposed of and the arterial blood collection element 14 can be interfaced with an arterial blood gas analysis instrument 80 for sample transfer and analysis.

The present disclosure provides an arterial blood module removably connectable to an arterial blood collection element. The arterial blood module includes a housing, a needle, a cap removably securable over the needle, a mixing chamber, and a safety shield engaged with a portion of the housing and transitionable from a first shield position in which a portion of the needle is exposed to a second shield position in which the needle is shielded by a portion of the safety shield. In one embodiment, the present disclosure includes an arterial blood collection system that includes an arterial blood collection element defining a collection chamber and an arterial blood module removably connectable to a portion of the arterial blood collection element.

In an exemplary embodiment, the arterial blood collection system of the present disclosure provides a novel blood collection device for collecting of arterial blood samples using a radial stick technique. The system of the present disclosure provides an efficient system that streamlines and reduces the number of workflow steps and enables single-handed device operation which allows for more efficient Arterial Blood Gas (ABG) collection procedures. The arterial blood module of the present disclosure includes ergonomic touch points, push button safety shield, automatic anticoagulant mixing and integrated vent cap for expelling air bubbles after a collection procedure, if necessary.

In an exemplary embodiment, the arterial blood module 16 of the present disclosure includes the open cell foam material 40. In other exemplary embodiments, the arterial blood collection element 14 could include the open cell foam material 40.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An arterial blood collection system, comprising:

an arterial blood collection element defining a collection chamber; and an arterial blood module removably connectable to a portion of the arterial blood collection element, the arterial blood module comprising:

a housing having a first end and a second end;

a needle extending from the first end, wherein the housing defines a vent chamber in communication with a fluid flow path defined between the needle and the arterial blood collection element, wherein the vent chamber is configured to expel air bubbles from the fluid flow path outside of the arterial blood module;

a cap removably securable over the needle;

a mixing chamber adjacent the second end; and a safety shield engaged with a portion of the housing and transitionable from a first shield position in which the safety shield is contained within the housing and a portion of the needle is exposed to a second shield position in which the needle is shielded by a portion of the safety shield.

2. The arterial blood collection system of claim 1, wherein the safety shield comprises:

a shield assembly; and an actuator transitionable from a first actuator position in which the actuator engages a portion of the shield assembly to lock the shield assembly in the first shield position to a second actuator position in which the actuator releases the shield assembly and the safety shield automatically moves to the second shield position.

3. The arterial blood collection system of claim 2, wherein the actuator comprises a push button.

4. The arterial blood collection system of claim 2, wherein the shield assembly comprises telescoping shields.

5. The arterial blood collection system of claim 2, wherein the shield assembly comprises:

a fixed outer shield;

a middle movable shield in communication with the fixed outer shield, wherein the middle movable shield moves relative to the fixed outer shield; and an inner movable shield in communication with the middle movable shield, wherein the inner movable shield moves relative to the middle movable shield.

6. The arterial blood collection system of claim 5, wherein with the safety shield in the first shield position, the inner movable shield is nested inside the middle movable shield, and the middle movable shield is nested inside the fixed outer shield.

7. The arterial blood collection system of claim 5, wherein with the safety shield in the second shield position, the inner movable shield extends from the middle movable shield, and the middle movable shield extends from the fixed outer shield.

8. The arterial blood collection system of claim 1, wherein the housing of the arterial blood module defines a flow channel from the first end to the second end.

9. The arterial blood collection system of claim 8, wherein the arterial blood module further comprises a sample stabilizer disposed within the flow channel between the first end of the housing and the mixing chamber.

10. The arterial blood collection system of claim 9, further comprising:

a material including pores disposed within the flow channel between the first end of the housing and the mixing chamber; and a dry anticoagulant powder within the pores of the material.

11. The arterial blood collection system of claim 10, wherein a blood sample dissolves and mixes with the dry anticoagulant powder while passing through the material.

12. The arterial blood collection system of claim 10, wherein the material is an open cell foam.

13. The arterial blood collection system of claim 10, wherein the sample stabilizer is the dry anticoagulant powder.

14. The arterial blood collection system of claim 1, wherein the arterial blood module further comprises a venting plug that allows air to pass therethrough and prevents a blood sample from passing therethrough, wherein a portion of the venting plug is in communication with the vent chamber.

15. The arterial blood collection system of claim 14, wherein the arterial blood module further comprises a first valve, and wherein, with the arterial blood module connected to the arterial blood collection element, the blood sample enters the collection chamber of the arterial blood collection element via the needle and the first valve.

16. The arterial blood collection system of claim 15, wherein the first valve allows the blood sample to pass from the arterial blood module to the collection chamber of the arterial blood collection element.

17. The arterial blood collection system of claim 16, wherein the first valve blocks the blood sample from passing from the collection chamber of the arterial blood collection element back to the arterial blood module.

18. The arterial blood collection system of claim 15, wherein the arterial blood module further comprises a second valve, and wherein, with the arterial blood module connected to the arterial blood collection element, air contained in the collection chamber of the arterial blood collection element and a portion of the blood sample enter the vent chamber via the second valve.

19. The arterial blood collection system of claim 18, wherein the air travels out of the arterial blood module via the venting plug.

20. The arterial blood collection system of claim 1, wherein the arterial blood module includes a first finger grip portion.

21. The arterial blood collection system of claim 20, wherein the arterial blood module includes a second finger grip portion, wherein the first finger grip portion is opposite the second finger grip portion.

22. The arterial blood collection system of claim 1, wherein the needle comprises thin wall needle technology.

23. The arterial blood collection system of claim 1, wherein the arterial blood collection element includes a plunger rod assembly including a stopper and a plunger rod.

24. An arterial blood module, comprising:

a housing having a first end and a second end;

a needle extending from the first end;

a cap removably securable over the needle;

a mixing chamber adjacent the second end, wherein the housing defines a vent chamber in communication with a fluid flow path defined between the needle and mixing chamber, wherein the vent chamber is configured to expel air bubbles from the fluid flow path outside of the arterial blood module; and a safety shield engaged with a portion of the housing and transitionable from a first shield position in which the safety shield is contained within the housing and a portion of the needle is exposed to a second shield position in which the needle is shielded by a portion of the safety shield.

25. The arterial blood module of claim 24, wherein the arterial blood module is removably connectable to a portion of an arterial blood collection element.

26. The arterial blood module of claim 25, wherein the arterial blood collection element defines a collection chamber.

27. An arterial blood collection system, comprising:

an arterial blood collection element defining a collection chamber; and an arterial blood module removably connectable to a portion of the arterial blood collection element, the arterial blood module comprising:

a housing having a first end and a second end;

a needle extending from the first end, wherein the housing defines a fluid flow path between the needle and the arterial blood collection element;

a cap removably securable over the needle;

a vent chamber in communication with the fluid flow path, wherein the vent chamber is configured to expel air bubbles from the fluid flow path outside of the arterial blood module;

a mixing chamber adjacent the second end; and a safety shield engaged with a portion of the housing and transitionable from a first shield position in which the safety shield is contained within the housing and a portion of the needle is exposed to a second shield position in which the needle is shielded by a portion of the safety shield.

28. The arterial blood collection system of claim 27, wherein the safety shield comprises:

a shield assembly; and an actuator transitionable from a first actuator position in which the actuator engages a portion of the shield assembly to lock the shield assembly in the first shield position to a second actuator position in which the actuator releases the shield assembly and the safety shield automatically moves to the second shield position.

29. The arterial blood collection system of claim 28, wherein the actuator comprises a push button.

* * * * *